(12) United States Patent
Konomura et al.

(10) Patent No.: US 9,766,159 B2
(45) Date of Patent: Sep. 19, 2017

(54) FIXTURE FOR ENDOSCOPIC INSPECTION

(71) Applicant: OLYMPUS CORPORATION, Shibuya-ku, Tokyo (JP)

(72) Inventors: Yutaka Konomura, Tachikawa (JP); Eiichi Kobayashi, Tama (JP); Fumio Hori, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 622 days.

(21) Appl. No.: 14/336,824

(22) Filed: Jul. 21, 2014

(65) Prior Publication Data

US 2015/0036130 A1     Feb. 5, 2015

(30) Foreign Application Priority Data

Aug. 1, 2013   (JP) .................. 2013-160750

(51) Int. Cl.

| | |
|---|---|
| *G01M 15/02* | (2006.01) |
| *G02B 23/24* | (2006.01) |
| *F01D 17/02* | (2006.01) |
| *F01D 21/00* | (2006.01) |
| *F01D 25/28* | (2006.01) |
| *G01N 21/954* | (2006.01) |

(52) U.S. Cl.
CPC ............ *G01M 15/02* (2013.01); *F01D 17/02* (2013.01); *F01D 21/003* (2013.01); *F01D 25/285* (2013.01); *G01N 21/954* (2013.01); *G02B 23/2476* (2013.01); *G02B 23/2484* (2013.01)

(58) Field of Classification Search
CPC .................................................... G01M 15/02
See application file for complete search history.

(56) References Cited

U.S. PATENT DOCUMENTS

| | | | |
|---|---|---|---|
| 4,298,312 | A | 11/1981 | MacKenzie et al. |
| 4,711,524 | A | 12/1987 | Morey et al. |
| 6,447,332 | B1 | 9/2002 | Djian |
| 7,518,632 | B2 | 4/2009 | Konomura |
| 8,314,834 | B2 | 11/2012 | Konomura |

(Continued)

FOREIGN PATENT DOCUMENTS

| | | |
|---|---|---|
| EP | 1739284 A2 | 1/2007 |
| JP | 03103810 A | 4/1991 |

(Continued)

OTHER PUBLICATIONS

Extended European Search Report dated Dec. 18, 2014 issued in counterpart European Application No. 14178326.6.

(Continued)

*Primary Examiner* — James Pontius
(74) *Attorney, Agent, or Firm* — Holtz, Holtz & Volek PC

(57) ABSTRACT

A fixture 4 for endoscopic inspection is provided with insertion direction regulating portions for regulating an access direction of an insertion portion of an endoscope fixed to an access port for an endoscope of an engine and connecting an external access port disposed on an exterior cover of the engine to an internal access port disposed on an exterior shroud of the engine and an installation direction regulating portion for uniquely regulating an installation direction so that the insertion direction regulating portions match the access direction at a time of attachment to the external access port.

3 Claims, 12 Drawing Sheets

(56) References Cited

U.S. PATENT DOCUMENTS

2006/0291998 A1* 12/2006 Dube .................... F01D 17/02
                                                                                          415/118
2010/0166537 A1    7/2010  Walker et al.
2013/0135457 A1    5/2013  Kell et al.

FOREIGN PATENT DOCUMENTS

| JP | 05297286 A | 11/1993 |
|---|---|---|
| JP | 2007163723 A | 6/2007 |

OTHER PUBLICATIONS

Japanese Office Action (and English translation thereof) dated May 9, 2017 issued in counterpart Japanese Application No. 2013-160750.

* cited by examiner

FIXTURE FOR ENDOSCOPIC INSPECTION

CROSS REFERENCE TO RELATED APPLICATION

This application claims benefit of Japanese Application No. 2013-160750 filed in Japan on Aug. 1, 2013, the entire contents of which are incorporated herein by this reference.

BACKGROUND OF THE INVENTION

1. Field of the Invention

The present invention relates to a fixture for endoscopic inspection which regulates an insertion direction of an endoscope and particularly relates to a fixture for endoscopic inspection installed in an inspection of a blade of an engine and the like.

2. Description of the Related Art

Recently, in inspecting a blade of a jet engine and the like, an endoscope device in which an insertion portion is inserted into the jet engine and a defect inspection of a blade is made by using a picked up inspection image of the blade is widely used.

Such a prior-art endoscope device technology is disclosed in Japanese Patent Application Laid-Open Publication No. 2007-163723, for example. In the Japanese Patent Application Laid-Open Publication No. 2007-163723, a technology of a fixture detachably installed in the vicinity of an access port provided in a jet engine when an insertion portion of an endoscope device is inserted into the jet engine is disclosed. This fixture is installed by bringing two pressing plates into contact with a wall surface of the jet engine and is fixed to the access port when the insertion portion of the endoscope device is inserted therein.

SUMMARY OF THE INVENTION

A fixture for endoscopic inspection according to an aspect of the present invention is a fixture for endoscopic inspection fixed to an access port for an endoscope of an engine, provided with an insertion direction regulating portion for regulating an access direction of an insertion portion of an endoscope connecting an external access port disposed on an exterior cover of the engine to an internal access port disposed on an exterior shroud of the engine and an installation direction regulating portion for uniquely regulating an installation direction so that the insertion direction regulating portion matches the access direction at a time of attachment to the external access port.

According to the present invention, the fixture for endoscopic inspection which can reliably regulate the insertion direction of the endoscope so that the insertion direction matches the access direction to the jet engine can be provided.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below by referring to the attached drawings.

Note that, in the following explanation, the figures based on the embodiment are schematic and a relationship between a thickness and a width of each portion, a ratio of thickness of the respective portions and the like are different from real ones, and even among the figures, those with different relationships of dimensions or different ratios might be included.

First, an endoscope system of an aspect of the present invention will be described below on the basis of the drawings.

Figure 1:
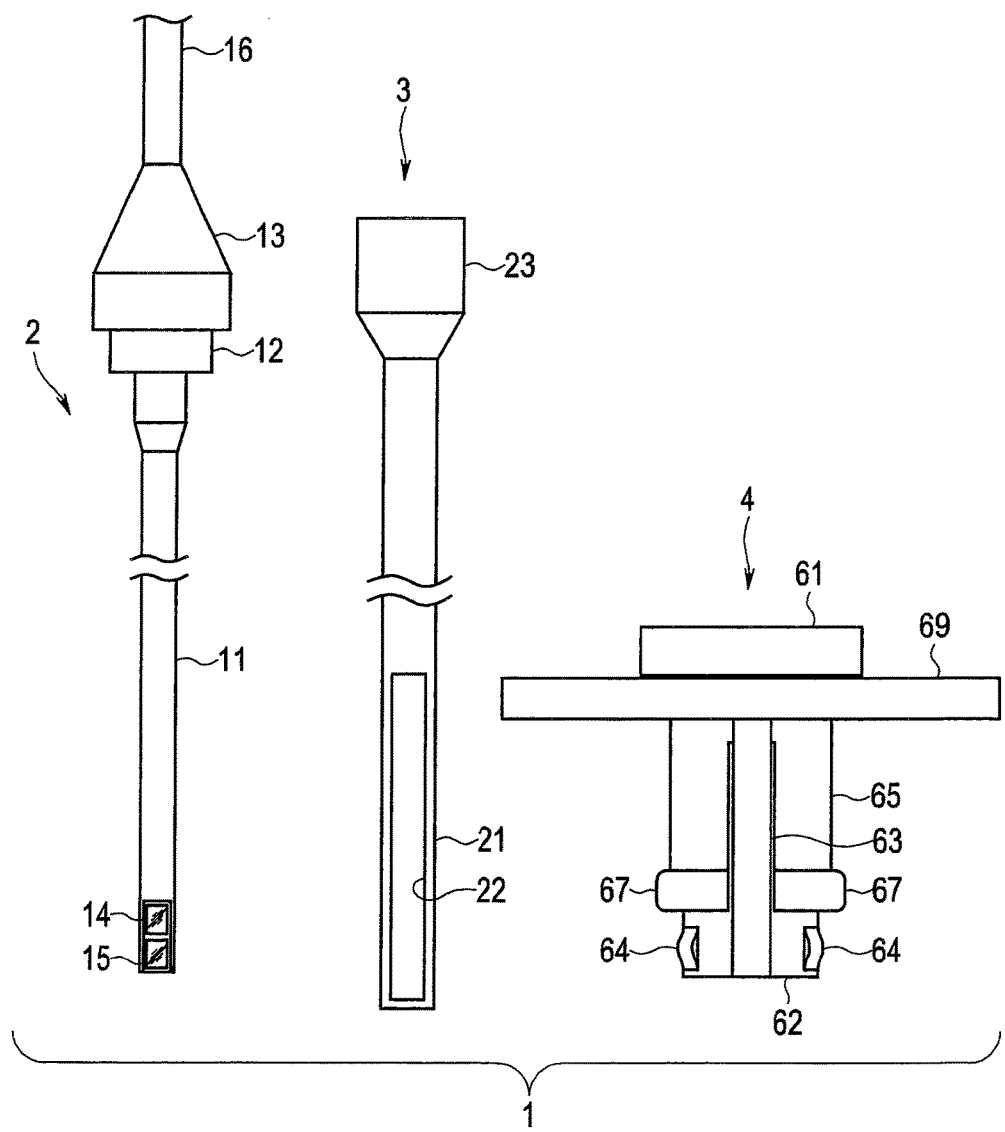
FIG. 1 is a side view illustrating a configuration of an endoscope system of an aspect of the present invention.
Figure 2:
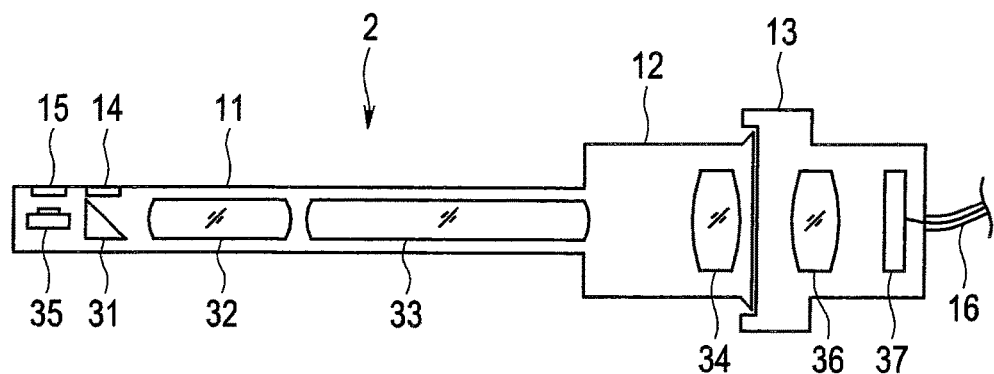
FIG. 2 is a diagram schematically illustrating configurations of a bore scope and an image pickup device of the aspect of the present invention.
Figure 3:
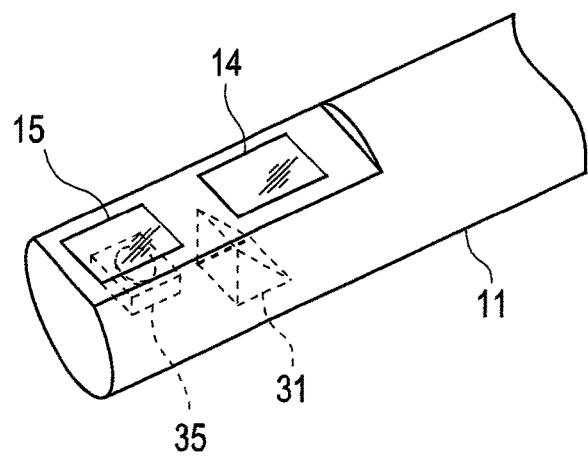
FIG. 3 is a perspective view illustrating a configuration of a tip end portion of an insertion portion of the bore scope of the aspect of the present invention.
Figure 4:
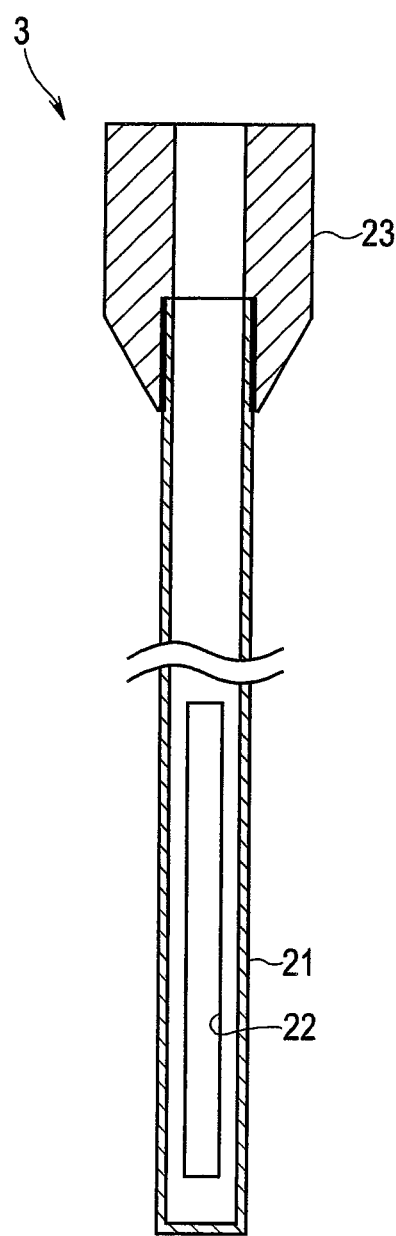
FIG. 4 is a sectional view illustrating a configuration of an endoscope guide device of the aspect of the present invention.
Figure 5:
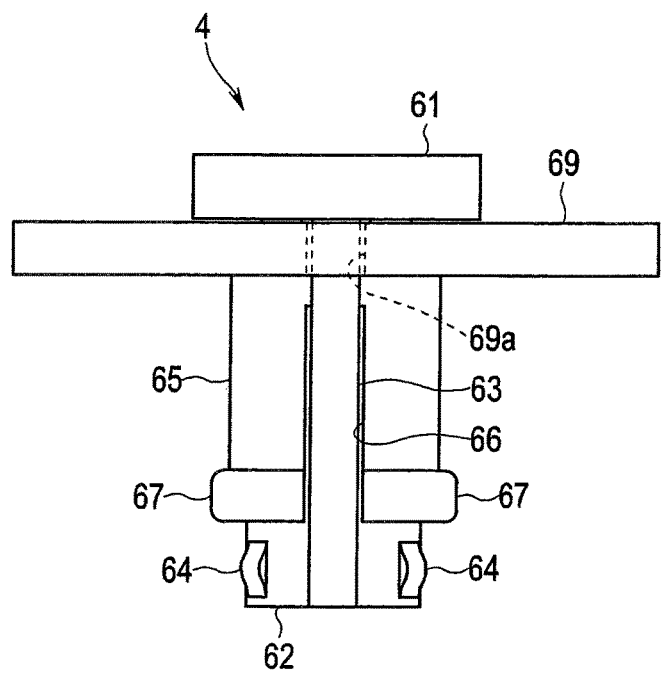
FIG. 5 is a side view illustrating a configuration of a fixture for endoscopic inspection of the aspect of the present invention.
Figure 6:
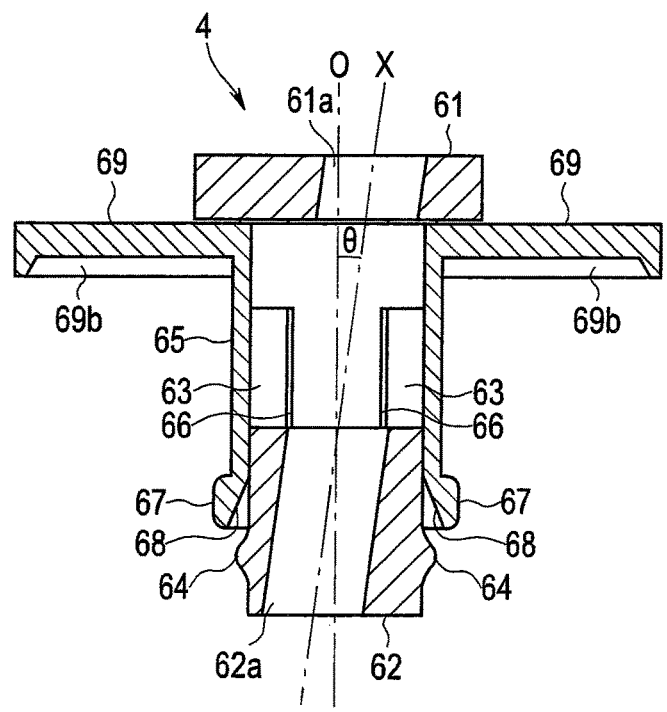
FIG. 6 is a sectional view illustrating the configuration of the fixture for endoscopic inspection of the aspect of the present invention.
Figure 7:
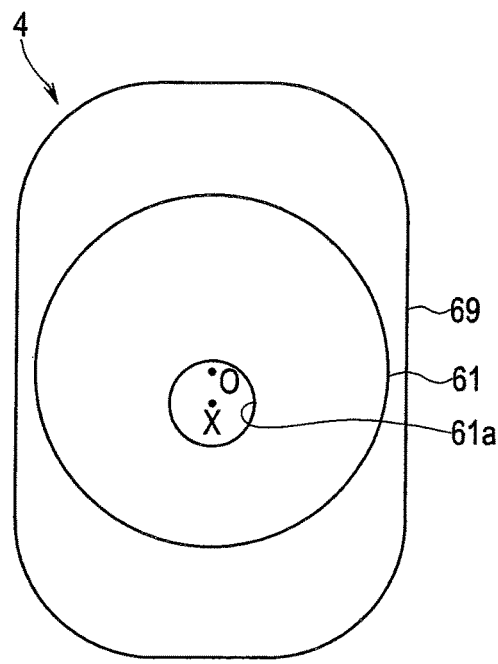
FIG. 7 is a plan view illustrating the configuration of the fixture for endoscopic inspection of the aspect of the present invention.
Figure 8:
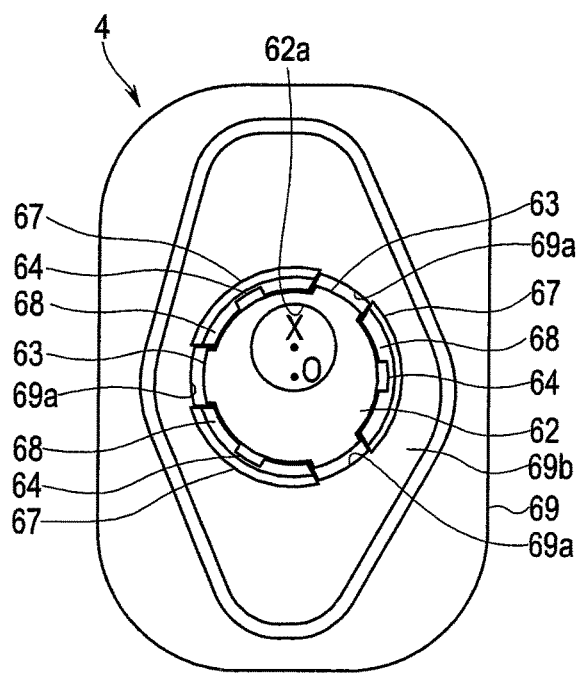
FIG. 8 is a bottom view illustrating the configuration of the fixture for endoscopic inspection of the aspect of the present invention.
Figure 9:
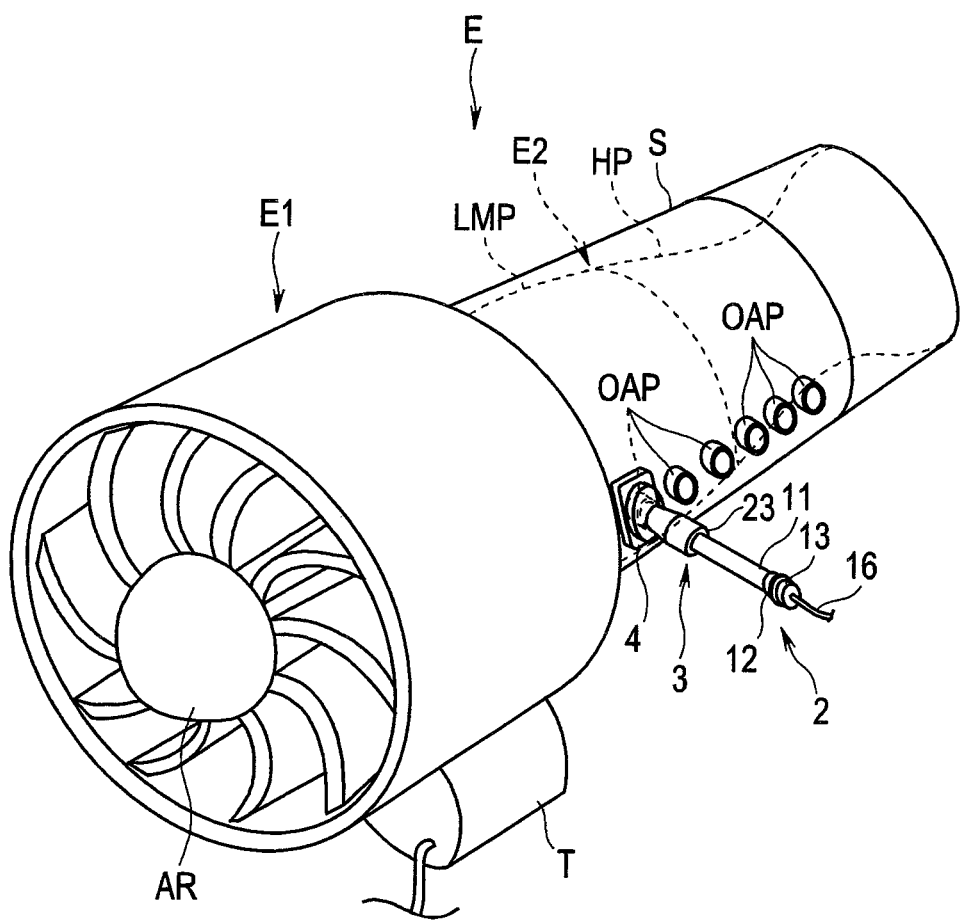
FIG. 9 is a perspective view illustrating a state of an inspection of a jet engine of the aspect of the present invention.
Figure 10:
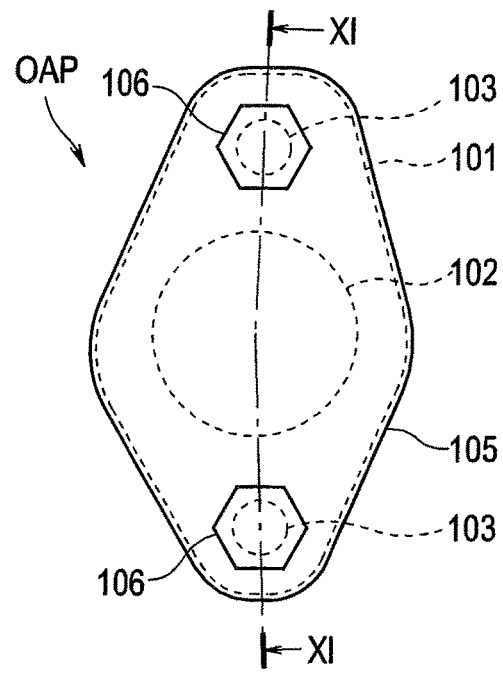
FIG. 10 is a plan view illustrating a configuration of an external access port of the aspect of the present invention.
Figure 11:
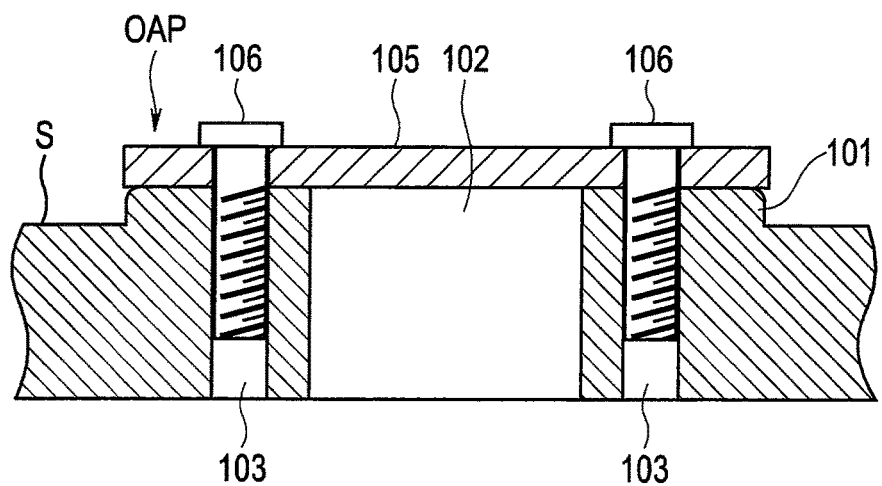
FIG. 11 is a sectional view illustrating the configuration of the external access port of the aspect of the present invention.
Figure 12:
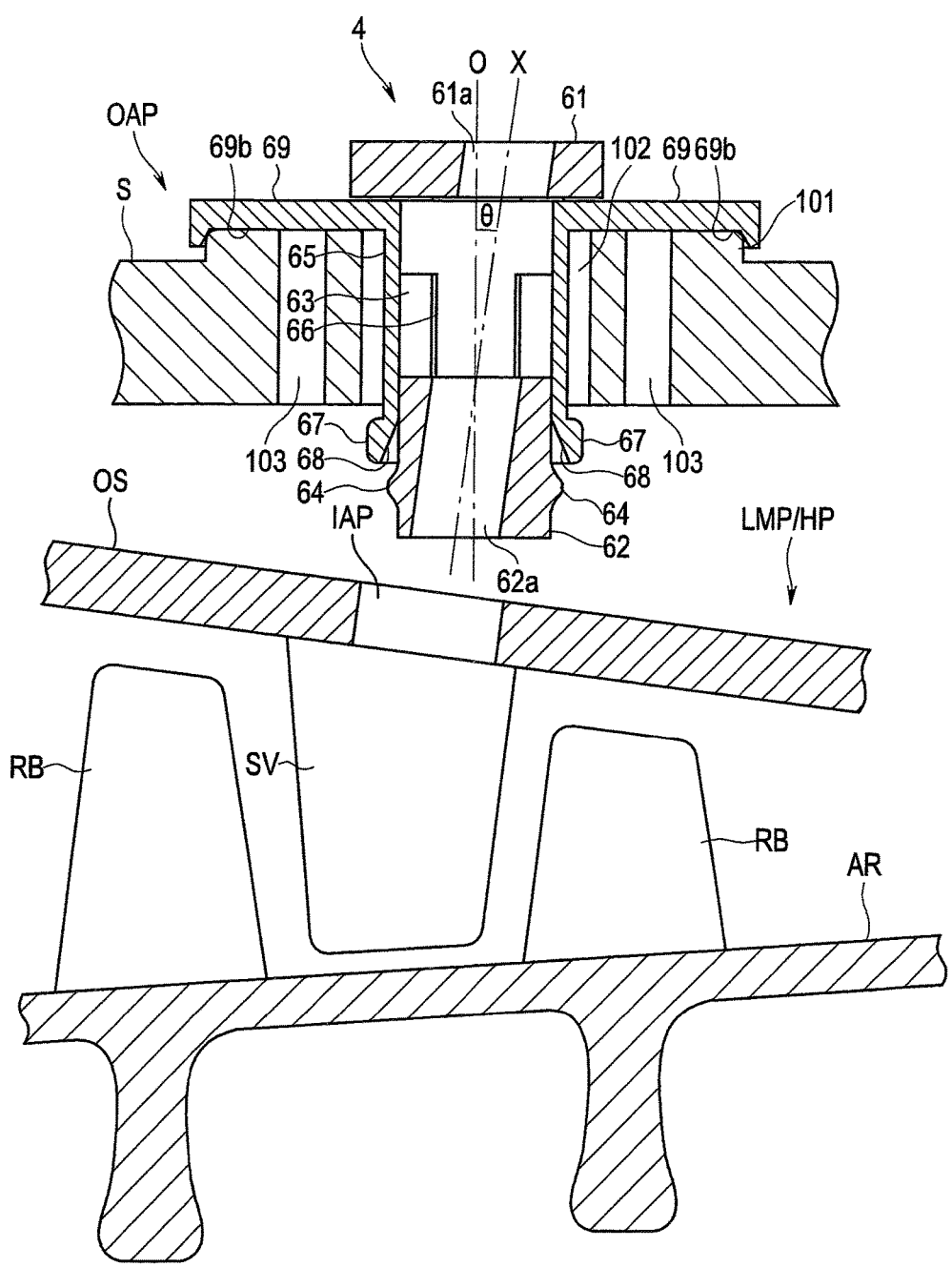
FIG. 12 is a sectional view illustrating a state in which the fixture for endoscopic inspection is inserted into the external access port of the aspect of the present invention.
Figure 13:
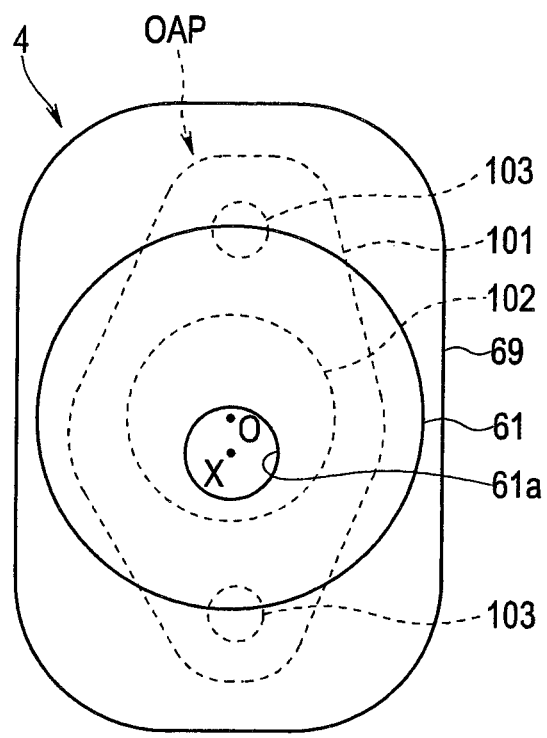
FIG. 13 is a plan view illustrating the state in which the fixture for endoscopic inspection is inserted into the external access port of the aspect of the present invention.
Figure 14:
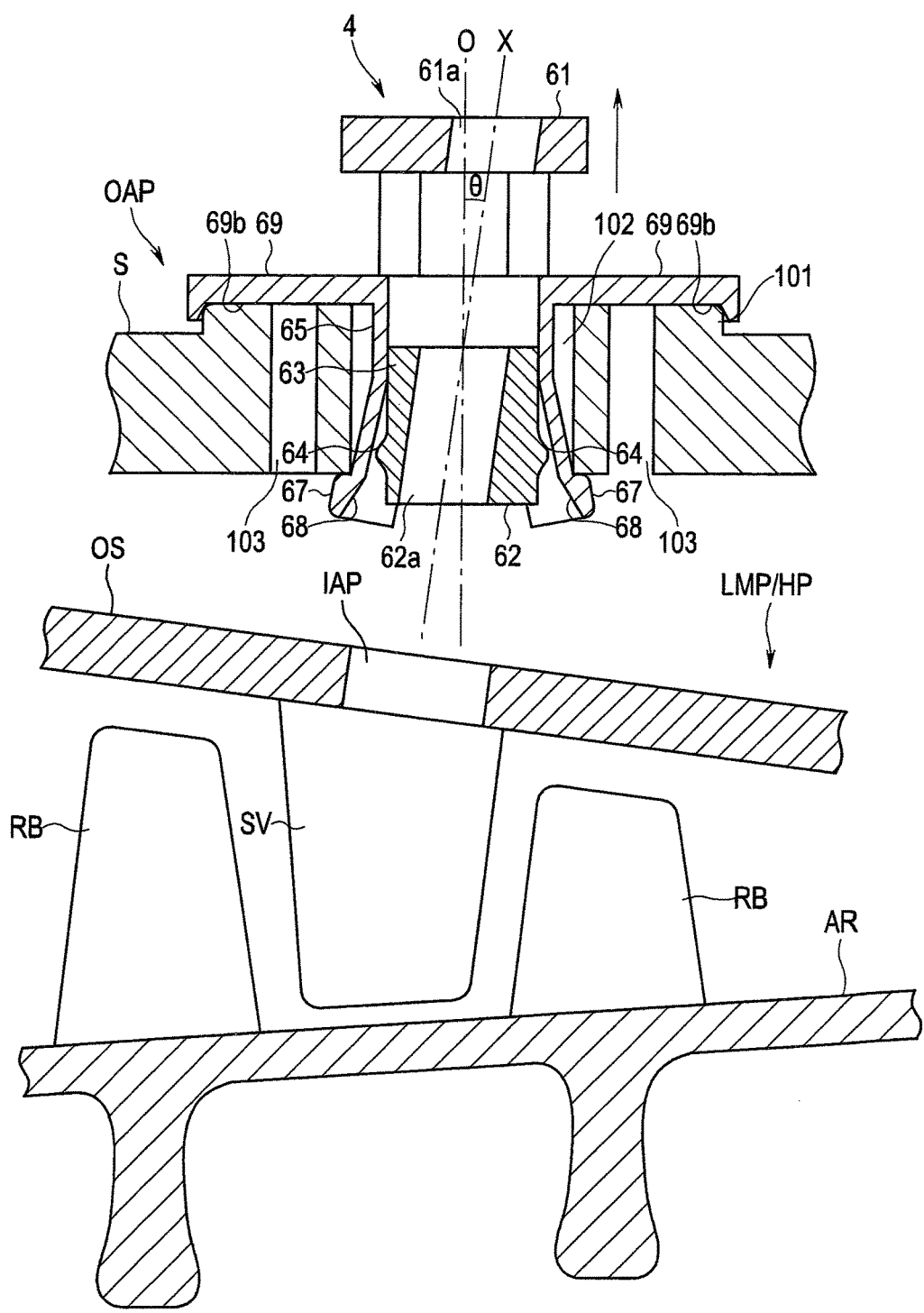
FIG. 14 is a sectional view illustrating the state in which the fixture for endoscopic inspection is fixed to the external access port of the aspect of the present invention.
Figure 15:
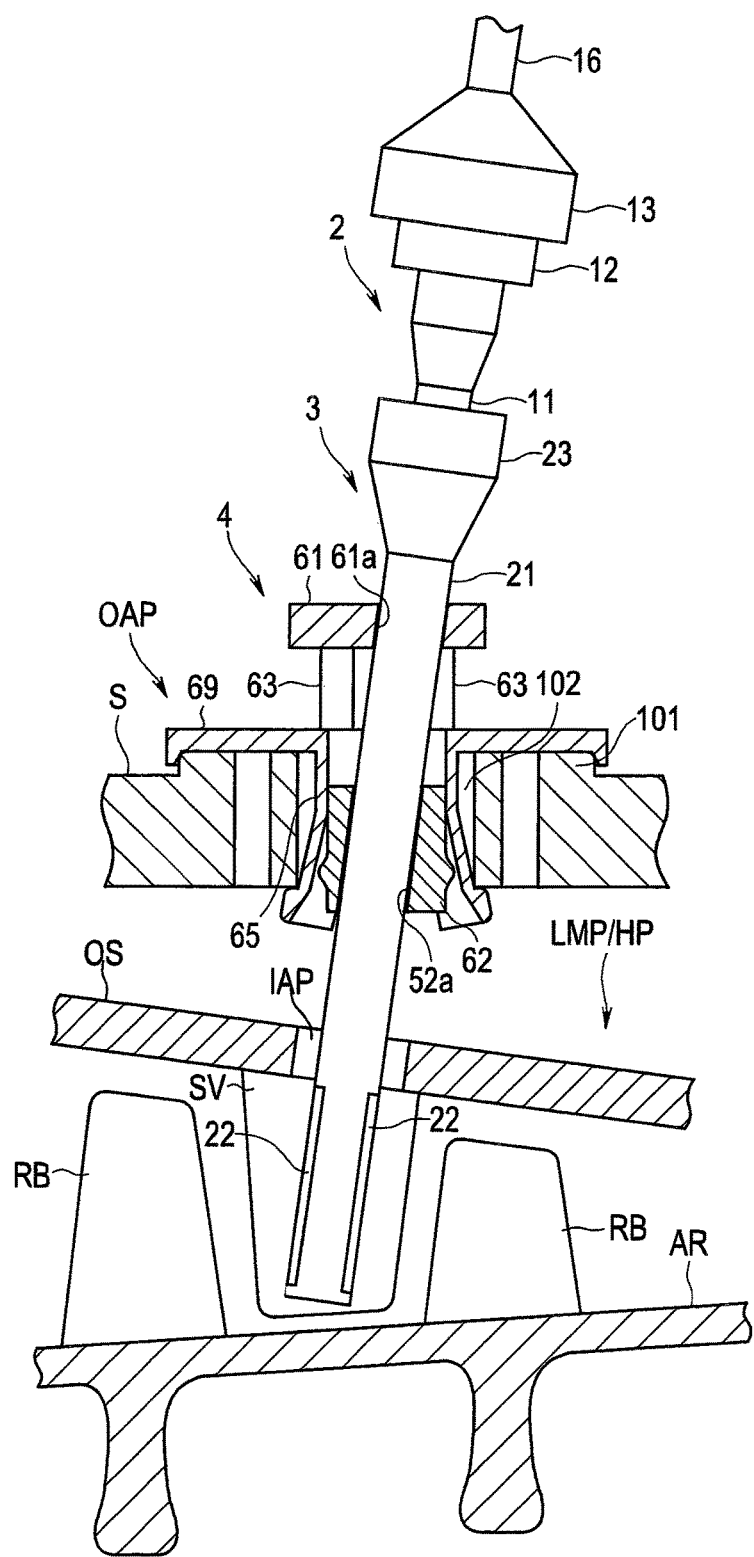
FIG. 15 is a sectional view illustrating a state in which the bore scope is inserted into the fixture for endoscopic inspection through the endoscope guide device of the aspect of the present invention.
Figure 16:
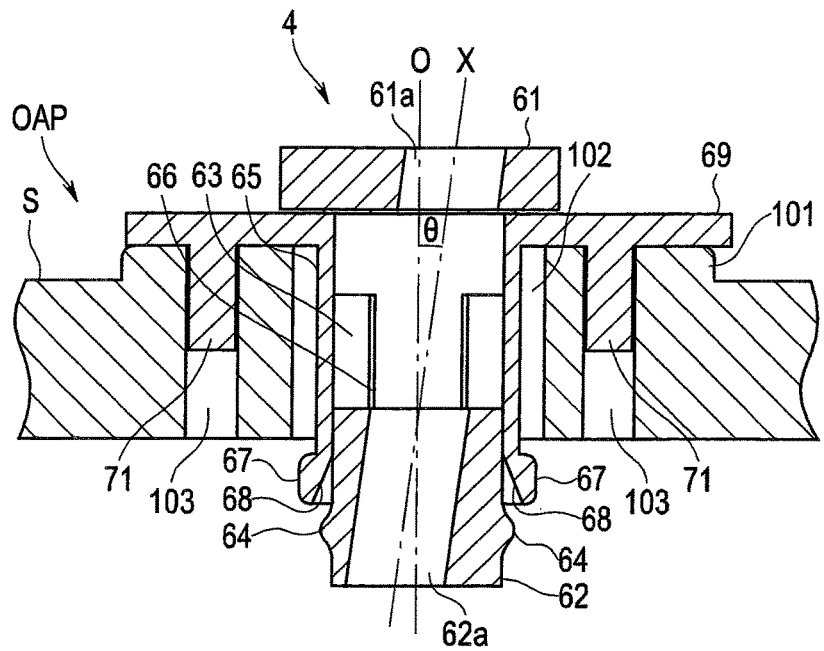
FIG. 16 is a sectional view illustrating the state in which the fixture for endoscopic inspection is inserted into an external access port of a first modification of the aspect of the present invention.
Figure 17:
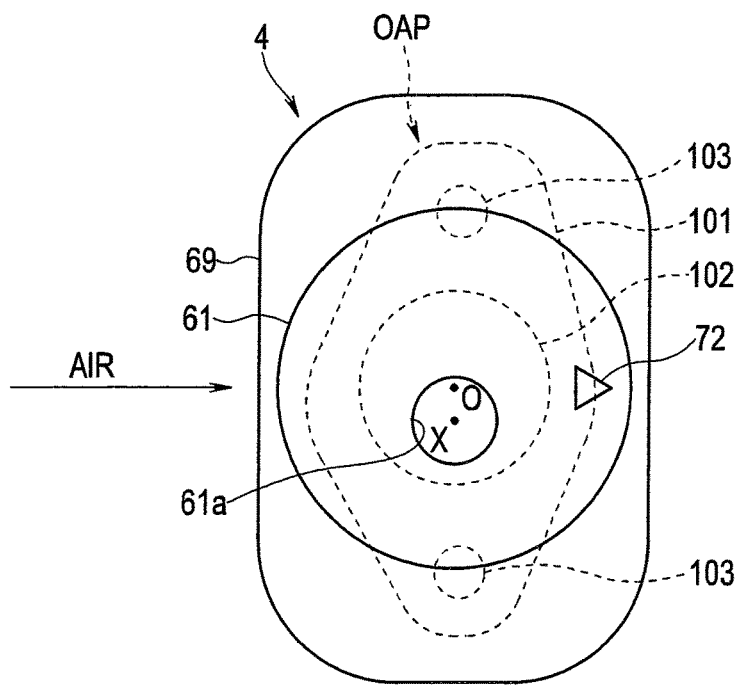
FIG. 17 is a plan view illustrating the state in which the fixture for endoscopic inspection is inserted into an external access port of a second modification of the aspect of the present invention.

FIG. 1 is a side view illustrating an entire configuration of an endoscope system, FIG. 2 is a diagram schematically illustrating configurations of a bore scope and an image pickup device, FIG. 3 is a perspective view illustrating a configuration of a tip end portion of an insertion portion of the bore scope, FIG. 4 is a sectional view illustrating a configuration of an endoscope guide device, FIG. 5 is a side view illustrating a configuration of a fixture for endoscopic inspection, FIG. 6 is a sectional view illustrating the configuration of the fixture for endoscopic inspection, FIG. 7 is a plan view illustrating the configuration of the fixture for endoscopic inspection, FIG. 8 is a bottom view illustrating the configuration of the fixture for endoscopic inspection, FIG. 9 is a perspective view illustrating a state of an inspection of a jet engine, FIG. 10 is a plan view illustrating a configuration of an external access port, FIG. 11 is a sectional view illustrating the configuration of the external access port, FIG. 12 is a sectional view illustrating a state in which the fixture for endoscopic inspection is inserted into the external access port, FIG. 13 is a plan view illustrating the state in which the fixture for endoscopic inspection is inserted into the external access port, FIG. 14 is a sectional view illustrating the state in which the fixture for endoscopic inspection is fixed to the external access port, FIG. 15 is a sectional view illustrating a state in which the bore scope is inserted into the fixture for endoscopic inspection through the endoscope guide device, FIG. 16 is a sectional view illustrating the state in which the fixture for endoscopic inspection is inserted into an external access port of a first variation of the aspect, and FIG. 17 is a plan view illustrating the state in which the fixture for endoscopic inspection is inserted into an external access port of a second variation.

An endoscope system 1 of the embodiment mainly includes, as illustrated in FIG. 1, a bore scope 2 as an endoscope, an endoscope guide device 3 to be inserted into a compressor portion of a jet engine and the like as an object for an inspection which will be described later, and a fixture 4 for endoscopic inspection into which the endoscope guide device 3 is inserted.

The bore scope 2, here, is a side-view type endoscope, and has a cylindrical insertion portion 11 in which an observation window 14 and an illumination window 15 are provided on a side part of a distal end portion and an eyepiece portion 12 disposed at a proximal end portion of the insertion portion 11. Note that, here, a detachable image pickup apparatus 13 is mounted to the eyepiece portion 12 of the bore scope 2.

Inside the bore scope 2, observing means and illuminating means are arranged. More specifically, as illustrated in FIGS. 2 and 3, in the insertion portion 11 of the bore scope 2, a mirror 31, an objective optical system 32, a relay optical system 33, and an LED 35 as the illuminating means, here, are arranged as an observation optical system. Note that, in the observation window 14 and the illumination window 15, transparent members such as glass are provided.

The mirror 31 is arranged in the distal end portion of the insertion portion 11. The mirror 31 is an optical member which leads light entering the insertion portion 11 from a side surface of the bore scope 2 in a direction of the eyepiece portion 12. The objective optical system 32 is arranged on a distal end side of the bore scope 2 in the insertion portion 11 and is an optical member for forming a real image of an object.

The LED 35 is an illumination light source emitting an illumination light toward the object and is connected to a wiring cable, not shown, disposed in the insertion portion 11, and a driving power is supplied by the wiring cable.

Note that the power for driving the LED 35 may be configured to be supplied from an outside, or a battery for supplying power may be configured to be provided in the bore scope 2. Moreover, the illuminating means is not limited to the LED 35, and the illumination light from an external light source may be configured to be transmitted by a light guide bundle.

In the eyepiece portion 12 of the bore scope 2, an eyepiece optical system 34 for visualizing an image transmitted by the relay optical system 33 is provided. In the image pickup apparatus 13 as a camera mounted on the eyepiece portion 12, an image pickup optical system 36 and a solid image pickup device 37 are arranged.

The image pickup optical system 36 forms an image of an object visualized by the eyepiece portion 12 of the bore scope 2. The solid image pickup device 37 picks up an image of the object formed by the image pickup optical system 36.

An image pickup signal which is a video signal photoelectrically converted in the solid image pickup device 37 is outputted to a personal computer (PC), not shown, via a signal cable 16. Note that the image pickup signal from the solid image pickup device 37 may be configured to be outputted to a video processor or the like via the signal cable 16.

Since the components of the bore scope 2 and the image pickup apparatus 13 described above are known, detailed explanation of the other components will be omitted.

Subsequently, the endoscope guide device 3 will be described below.

The endoscope guide device 3 mainly includes an insertion portion guide tube 21 and a grasping portion 23 connected to a proximal end of the insertion portion guide tube 21 as illustrated in FIG. 4.

The insertion portion guide tube 21 is a rigid tube made of metal or the like with a distal end side closed into which the insertion portion 11 of the bore scope 2 can be removably inserted. Note that the grasping portion 23 has an outer diameter larger than the insertion portion guide tube 21 so as to be grasped easily by a user.

The insertion portion guide tube 21 has two observation opening portions 22 faced with each other as long holes along a longitudinal direction on a side peripheral portion from the distal end side to the middle (only one of them is shown in FIG. 4). These two observation opening portions 22 are window portions for enabling observation of an object by the bore scope 2 in a state in which the insertion portion 11 of the bore scope 2 is inserted into the insertion portion guide tube 21.

That is, the bore scope 2 becomes capable of observing an object by the bore scope 2 without a view field interfered by the insertion portion guide tube 21 with the observation window 14 and the illumination window 15 exposed from the observation opening portion 22.

Subsequently, the fixture 4 for endoscopic inspection of the embodiment will be described below.

The fixture 4 for endoscopic inspection illustrated FIGS. 5 to 8 (hereinafter referred to simply as a fixture for endoscopic inspection) includes a first columnar portion 61, a plurality of or three, here, arm portions 63 (only one of them is shown in FIG. 5), a second columnar portion 62, and a fixed cylinder portion 65.

Note that the three arm portions 63 are extended at substantially equal intervals around a periphery from the first columnar portion 62. Extended end portions of these three arm portions 63 are fixed to an outer peripheral portion of the second columnar portion.

The fixed cylinder portion 65 is disposed between the first columnar portion 61 and the second columnar portion 62 and disposed capable of advance/retreat so as to be fitted in inner sides of the three arm portions 63.

That is, in the fixture 4 for endoscopic inspection, the second columnar portion 62 is connected by the three arm portions 63 extended from the first columnar portion 61, and the fixed cylinder portion 65 is disposed in the insides of these three arm portions 63.

In the first columnar portion 61, a first insertion hole 61a which is an insertion direction regulating portion formed having a hole axis X with a predetermined angle formed with respect to a center axis O (see FIGS. 6 and 7) is formed. That is, in the first insertion hole 61a, the hole axis X with the predetermined angle θ is set to the center axis O in a longitudinal direction of the fixture 4 for endoscopic inspection.

In the second columnar portion 62, three, here, projecting portions 64 (only two of them are shown in FIG. 5) projecting to an outer diameter direction are formed at substantially equal intervals on the outer peripheral portion. In the second columnar portion 62, too, a second insertion hole 62a which is an insertion direction regulating portion formed having the hole axis X with the predetermined angle θ with respect to a center axis O (see FIGS. 6 and 8) is formed. That is, in the second insertion hole 62a, too, the hole axis X with the predetermined angle θ is set to the center axis O in a longitudinal direction of the fixture 4 for endoscopic inspection, and the second insertion hole 62a also has the hole axis X coaxial with the first insertion hole 61a.

The fixed cylinder portion 65 has three notch portions 66 formed from one of end portions which becomes the second columnar portion 62 side at positions along the arm portions 63 to the middle portion, respectively. Moreover, the fixed cylinder portion 65 has a diameter expanded portion 67 projecting to the outer diameter direction on the outer peripheral portion of the end portion on the second columnar portion 62 side.

Then, in the fixed cylinder portion 65, on an inner surface side of the diameter expanded portion 67, a taper 68 (see FIG. 6) is formed so as to expand in the one end portion direction on the second columnar portion 62 side.

In the fixed cylinder portion 65, an outward flange 69 is provided on an end portion on a side of the first columnar portion 61. In the outward flange 69, hole portions 69a into which the three arm portions 63 are inserted and an engagement recess portion 69b (see FIGS. 6 and 8) as an installation direction regulating portion is formed on a surface on the second columnar portion 62 side.

The engagement recess portion 69b has a shape similar to a projecting shape of an external access port OAP provided on a skin S of a jet engine E, not shown, here, which will be described later. Note that a configuration of the external access port OAP will be described later.

In the endoscope system 1 of the embodiment configured as above, the fixture 4 for endoscopic inspection is mounted on the jet engine E which is an object for an inspection (hereinafter referred to simply as an engine) as illustrated in FIG. 9, and the endoscope guide device 3 is inserted into the fixture 4 for endoscopic inspection.

Then, into the insertion portion guide tube 21, the insertion portion 11 of the bore scope 2 is inserted, and an endoscopic inspection of a plurality of blades (hereinafter referred to as a rotor blade RB or a stator vane SV in some cases) inside the engine E which is an inspection target is conducted.

Here, the engine E will be described in brief.

The engine E has, as illustrated in FIG. 9, an intake portion E1, a compressor portion E2, a combustion portion, and an exhaust portion (neither is not shown in detail) from the intake side toward the exhaust side.

The compressor portion E2 is covered by a cylindrical skin S which becomes an exterior cover. The compressor portion E2 is an axial-flow type compressor and has a plurality of stages, in which a low-to-medium pressure compressor portion LMP and a high-pressure compressor portion HP are arranged in order from the intake side toward the exhaust side therein.

In the skin S, a plurality of or six, here, external access ports OAP as access ports for endoscope on which the fixtures 4 for endoscopic inspection are installed, respectively, are provided. Into the fixtures 4 for endoscopic inspection installed on these external access ports OAP, respectively, the insertion portion guide tubes 21 of the endoscope guide devices 3 are inserted. Then, the bore scope 2 is inserted into the compressor portion E2 through the insertion portion guide tube 21.

As described above, the endoscope system 1 inspects the plurality of rotor blades RB or stator vanes SV (neither is not shown, see FIG. 12 and the like) in the compressor portion E2 of the engine E by the endoscope guide device 3 and the bore scope 2 inserted into the fixture 4 for endoscopic inspection.

The endoscopic inspection is conducted by connecting a turning tool T to the engine E. The turning tool T is a device for rotating a rotating shaft AR, includes a motor and a gearbox, and can rotate the rotating shaft AR through a shaft (not shown).

Then, in the endoscopic inspection, while the plurality of rotor blades which will be described later are rotated around the rotating shaft AR by using the turning tool T, the plurality of rotor blades provided on the rotating shaft AR are photographed by the bore scope 2 inserted into the compressor portion E2 and the endoscopic inspection is conducted.

On the external access port OAP provided on the skin S, a convex portion 101 projected and formed from the surface is provided as illustrated in FIGS. 10 and 11. At a center of the convex portion 101, an access hole portion 102 as a hole portion is drilled. Moreover, on both sides of the access hole portion 102, two screw holes 103 for bolt tightening are formed.

On the external access port OAP, a lid body 105 covering the access hole portion 102 is mounted when an endoscopic inspection is not conducted. The lid body 105 is fastened by screwing bolts 106 into the two screw holes.

Here, an operation of fixing the fixture 4 for endoscopic inspection which regulates an insertion direction of the endoscope guide device 3 to the compressor portion E2 of the engine E by installing the fixture 4 for endoscopic inspection on the external access port OAP on the skin S in an endoscopic inspection conducted by the endoscope system 1 of the embodiment will be described.

First, the lid body 105 of the external access port OAP on the skin S is removed. Then, the fixture 4 for endoscopic inspection is inserted into the access hole portion 102 of the external access port OAP on the skin S from the second columnar portion 62 side.

At this time, in the fixture 4 for endoscopic inspection, as illustrated in FIG. 12, the fixed cylinder portion 65 is inserted into the access hole portion 102 to a position where the outward flange 69 is brought into contact with the convex portion 101 of the external access port OAP.

Note that, in the fixture 4 for endoscopic inspection, as illustrated in FIG. 13, a direction around the center axis O is adjusted to a correct position so that a shape of the engagement recess portion 69b formed on the outward flange 69 matches a shape of the convex portion 101 of the external access port OAP, and the engagement recess portion 69b and the convex portion 101 are engaged with each other.

From this state, in the fixture 4 for endoscopic inspection, the first columnar portion 61 is pulled so that the second columnar portion 62 slides and enters into the fixed cylinder portion 65, and as illustrated in FIG. 14, a diameter of one of end portions of the fixed cylinder portion 65 on the second columnar portion 62 side is expanded.

More specifically, in the fixture 4 for endoscopic inspection, if the first columnar portion 61 is pulled, the second columnar portion 62 slides with the three arm portions 63 and enters into the fixed cylinder portion 65.

At this time, the second columnar portion 62 smoothly enters into the fixed cylinder portion 65 by the taper 68 of the fixed cylinder portion 65, and each of the three projecting portions 64 is brought into contact with an inner peripheral surface of the fixed cylinder portion 65. Then, in the fixed cylinder portion 65, three end piece portions divided by the three notch portions 66 are diameter-expanded in the outer diameter direction by contact of each of the projecting portions 64 with the inner peripheral surface.

As a result, the fixture 4 for endoscopic inspection sandwiches an outer surface and an inner surface around the access hole portion 102 of the external access port OAP provided on the skin S by the outward flange 69 and the three diameter expanded portions 67 of the fixed cylinder portion 65.

That is, when the first columnar portion 61 is pulled, the second columnar portion 62 slides with the three arm portions 63 and enters into the fixed cylinder portion 65, and the three end piece portions divided by the three notch portions 66 are diameter-expanded in the outer diameter direction.

Then, the outward flange 69 of the fixed cylinder portion 65 is abutted on the outer surface of the convex portion 101 around the access hole portion 102 of the external access port OAP, the diameter expanded portion 67 formed on the diameter-expanded three end piece portions of the fixed cylinder portion 65 is caught by the inner surface around the access hole portion 102 of the external access port OAP, and the fixture 4 for endoscopic inspection is fixed to the external access port OAP so that the thickness direction of the skin S is sandwiched by the outward flange 69 and the three diameter expanded portions 67. As a result, the fixture 4 for endoscopic inspection is firmly fixed to the external access port OAP.

As described above, since the engagement recess portion 69b formed on the outward flange 69 is engaged with the convex portion 101 of the external access port OAP, the fixture 4 for endoscopic inspection is positioned in a state in which the insertion direction into the access hole portion 102 of the external access port OAP is regulated. Then, the fixture 4 for endoscopic inspection is fixed to the external access port OAP since the first columnar portion 61 is pulled toward a hand side.

In this state, the first insertion hole 61a and the second insertion hole 62a formed in the first columnar portion 61 and the second columnar portion 62 of the fixture 4 for endoscopic inspection are regulated so that an extension of the common hole axis X passes in the vicinity of the opening center of the hole portion of an internal access port IAP as an access port for an endoscope formed on an exterior shroud OS of the low-to-medium pressure compressor portion LMP or the high-pressure compressor portion HP of the engine E.

Then, into the first insertion hole 61a and the second insertion hole 62a of the fixture 4 for endoscopic inspection, as illustrated in FIG. 15, the insertion portion guide tube 21 of the endoscope guide device 3 is inserted, and the insertion portion 11 of the bore scope 2 is inserted into the insertion portion guide tube 21. As described above, an endoscopic inspection of the stator vane SV or the rotor blade RB in the low-to-medium pressure compressor portion LMP or the high-pressure compressor portion HP is conducted.

As described above, in the endoscope system 1 of the embodiment, when the fixture 4 for endoscopic inspection is fixed to the external access port OAP, the engagement recess portion 69b of the outward flange 69 is engaged with the convex portion 101 of the external access port OAP, whereby the installation direction of the fixture 4 for endoscopic inspection is uniquely determined, and an access direction of inserting the insertion portion guide tube 21 and the bore scope 2 of the endoscope guide device 3 into the low-to-medium pressure compressor portion LMP or the high-pressure compressor portion HP of the engine E is regulated by the first insertion hole 61a and the second insertion hole 62a.

That is, by being inserted into the first insertion hole 61a and the second insertion hole 62a of the fixture 4 for endoscopic inspection, the insertion portion guide tube 21 of the endoscope guide device 3 can be smoothly inserted without being brought into contact with the internal access port IAP of the exterior shroud OS, contact or being caught.

Therefore, in the endoscope system 1, even if the hole axes of the external access port OAP provided on the skin S side of the engine E and the internal access port IAP provided on the exterior shroud OS side are not coaxial but have a predetermined angle, by inserting the endoscope guide device 3 in the access direction connecting the external access port OAP and the internal access port IAP, the access direction of the bore scope 2 can be easily positioned by the fixture 4 for endoscopic inspection.

As a result, in the fixture 4 for endoscopic inspection, the insertion direction of the bore scope 2 can be reliably regulated through the endoscope guide device 3 so that the insertion direction matches the access direction into the engine E.

Note that a shape of the convex portion 101 of the external access port OAP of the engine E might be different depending on a model of the engine E or a spot of each of the external access ports OAP in the same engine E.

Thus, the shape of the engagement recess portion 69b formed on the outward flange 69 of the fixture 4 for endoscopic inspection is set individually so as to match the respective shapes exclusively.

Moreover, the access direction of the bore scope 2 into the engine E might be different also depending on the model of the engine E or a combination spot of each of the external access ports OAP and each of the internal access ports IAP in the same engine E.

Thus, an inclination angle (the above described predetermined angle θ) of the first insertion hole 61a and the second insertion hole 62a as the insertion direction regulating portion formed on the fixture 4 for endoscopic inspection is set as appropriate in accordance with the model of the engine E or the combination spot of each of the external access ports OAP and each of the internal access ports IAP.

That is, the inclination angle of the first insertion hole 61a and the second insertion hole 62a as the insertion direction regulating portion formed on the fixture 4 for endoscopic inspection is set as appropriate in accordance with the access direction connecting the external access port OAP and the internal access port IAP.

Moreover, the configuration in which the bore scope 2 is inserted into the first insertion hole 61*a* and the second insertion hole 62*a* of the fixture 4 for endoscopic inspection through the endoscope guide device 3 is exemplified in the above, but this is not limiting, and the bore scope 2 may be inserted directly into the first insertion hole 61*a* and the second insertion hole 62*a* of the fixture 4 for endoscopic inspection. Moreover, the fixture 4 for endoscopic inspection and the insertion portion guide tube 21 may be integrated.

Modifications

Note that the fixture 4 for endoscopic inspection of the embodiment may be as follows in relation with the configuration of the installation direction regulating portion for uniquely positioning the installation direction into the external access port OAP.

First Modification

As illustrated in FIG. 16, in the fixture 4 for endoscopic inspection of this modification, the engagement recess portion 69*b* is not formed on the outward flange 69, and two projecting portions 71 as installation direction regulating portions engageably inserted into the two screw holes 103 for bolt tightening of the external access port OAP provided on the skin S are provided on the outward flange 69. These two projecting portions 71 are extended in a direction of the second columnar portion 62 from a rear surface side faced with the surface of the convex portion 101 of the outward flange 69.

In the fixture 4 for endoscopic inspection configured as above, when the fixed cylinder portion 65 is inserted into the access hole portion 102 of the external access port OAP, by engageably inserting the two projecting portions 71 in the screw holes 103, respectively, the direction around the center axis O is adjusted to a correct position.

Then, in the fixture 4 for endoscopic inspection, the outward flange 69 is inserted into the access hole portion 102 to a position in contact with the convex portion 101 of the external access port OAP.

After that, in the fixture 4 for endoscopic inspection, the first columnar portion 61 is pulled so that the second columnar portion 62 slides and enters into the fixed cylinder portion 65 and fixed to the external access port OAP as described above.

With such configuration, too, in this modification, when the fixture 4 for endoscopic inspection is fixed to the external access port OAP, each of the two projecting portions 71 is engageably inserted into the screw hole 103, whereby the installation direction of the fixture 4 for endoscopic inspection is uniquely determined. As a result, the access direction of inserting the insertion portion guide tube 21 and the bore scope 2 of the endoscope guide device 3 into the low-to-medium pressure compressor portion LMP or the high-pressure compressor portion. HP of the engine E is regulated by the first insertion hole 61*a* and the second insertion hole 62*a* of the fixture 4 for endoscopic inspection.

Note that the configuration of the fixture 4 for endoscopic inspection of this modification is based on the configuration in which the two screw holes 103 for bolt tightening of the external access port OAP are not provided point symmetric to the center axis of the access hole portion 102 (common to the center axis O of the fixture 4 for endoscopic inspection to be installed).

Second Modification

As illustrated in FIG. 17, in the fixture 4 for endoscopic inspection, a correct position where the fixed cylinder portion 65 is inserted into the access hole portion 102 of the external access port OAP may be regulated by providing a mark 72 as an index portion which becomes an installation direction regulating portion on a surface of the first columnar portion 61 and by matching this mark 72 with a flow direction of air (indicated by an arrow) flowing from an intake side toward an exhaust side of the engine E.

That is, in the fixture 4 for endoscopic inspection, when the fixed cylinder portion 65 is inserted into the access hole portion 102 of the external access port OAP, the direction around the center axis O can be adjusted to a correct position by matching the mark 72 to the flow direction of the air of the engine E.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A fixture for endoscopic inspection which is to be fixed to an access port of an engine for access by an endoscope, the fixture comprising:
   an insertion direction regulating portion for regulating an access direction of an insertion portion of an endoscope connecting an external access port disposed on an exterior cover of the engine to an internal access port disposed on an exterior shroud of the engine; and
   an installation direction regulating portion for uniquely regulating an installation direction so that the insertion direction regulating portion matches the access direction at a time of attachment to the external access port,
   wherein the installation direction regulating portion is an index; and
   the index is arranged such that, by matching the index with a flow direction of air of the engine, the installation direction is uniquely regulated so that the installation direction matches the access direction.

2. The fixture for endoscopic inspection according to claim 1, wherein the insertion direction regulating portion includes a first hole axis having a predetermined angle with respect to a center axis in a longitudinal direction of a fixed cylinder portion connected to the installation direction regulating portion, the fixed cylinder portion being configured to be inserted into the external access port.

3. The fixture for endoscopic inspection according to claim 2, wherein the insertion direction regulating portion includes a first insertion hole and a second insertion hole, and the first hole axis of the first insertion hole and a second hole axis of the second insertion hole are coaxial.

* * * * *